United States Patent
Yoshikawa et al.

(10) Patent No.: US 8,562,531 B2
(45) Date of Patent: Oct. 22, 2013

(54) ULTRASONIC MOTION DETECTING DEVICE, AND IMAGE PRODUCING DEVICE AND ULTRASONIC THERAPEUTIC USING THE DETECTING DEVICE

(75) Inventors: Hideki Yoshikawa, Kokubunji (JP); Takashi Azuma, Kawasaki (JP); Shin-ichiro Umemura, Muko (JP); Ken-ichi Kawabata, Kodaira (JP)

(73) Assignee: Hitachi Medical Corporation, Tokyo (JP)

( * ) Notice: Subject to any disclaimer, the term of this patent is extended or adjusted under 35 U.S.C. 154(b) by 1155 days.

(21) Appl. No.: 10/583,033

(22) PCT Filed: Nov. 16, 2004

(86) PCT No.: PCT/JP2004/016974
§ 371 (c)(1),
(2), (4) Date: Jun. 15, 2006

(87) PCT Pub. No.: WO2005/058168
PCT Pub. Date: Jun. 30, 2005

(65) Prior Publication Data
US 2007/0078326 A1 Apr. 5, 2007

(30) Foreign Application Priority Data
Dec. 16, 2003 (JP) ................................. 2003-417436

(51) Int. Cl.
*A61B 8/00* (2006.01)
(52) U.S. Cl.
USPC ........................... 600/439; 600/407; 600/437
(58) Field of Classification Search
USPC .................. 600/439, 437, 454, 441, 456, 449
See application file for complete search history.

(56) References Cited

U.S. PATENT DOCUMENTS 4,671,293 A * 6/1987 Shaulov ........................ 600/447
4,932,414 A * 6/1990 Coleman et al. .............. 600/445
(Continued)

FOREIGN PATENT DOCUMENTS

JP 09-024034 1/1997
JP 11-262489 9/1999
(Continued)

OTHER PUBLICATIONS

Newhouse V L et al, "Three-Dimensional Vector Flow Estimation Using Two Transducers and Spectral Width", IEEE Transactions on Ultrasonics Ferroelectrics and Frequency Control, IEEE US vol. 41, No. 1, Jan. 1, 2994 pp. 90-95 XP000442119.
(Continued)

*Primary Examiner* — Tse Chen
*Assistant Examiner* — Joel F Brutus
(74) *Attorney, Agent, or Firm* — Antonelli, Terry, Stout & Kraus, LLP.

(57) ABSTRACT

There is provided a ultrasonic motion detecting device that detects a three-dimensional motion of an object. The ultrasonic motion detecting device, comprises first and second ultrasonic transducers 13 having piezoelectric elements arranged in an array, which transmit ultrasonic waves to an object and acquire reflection signals from the object, a motion detection unit 20 that extracts an estimation region which is used for estimating a motion of the object from the reflection signals that are acquired by the first and second ultrasonic transducers, and detects a three-dimensional motion within the estimation region, and an image display unit 19 that displays the three-dimensional motion within the estimation region, wherein ultrasonic wave scanning surfaces due to the first and second ultrasonic transducers cross over each other.

20 Claims, 11 Drawing Sheets

(56) References Cited

U.S. PATENT DOCUMENTS

| | | | |
|---|---|---|---|
| 5,435,311 A | 7/1995 | Umemura et al. | |
| 5,474,073 A * | 12/1995 | Schwartz et al. | 600/456 |
| 5,734,441 A * | 3/1998 | Kondo et al. | 348/700 |
| 5,766,129 A * | 6/1998 | Mochizuki | 600/443 |
| 5,769,079 A | 6/1998 | Hossack | |
| 5,873,830 A * | 2/1999 | Hossack et al. | 600/447 |
| 5,910,118 A * | 6/1999 | Kanda et al. | 600/455 |
| 6,014,473 A * | 1/2000 | Hossack et al. | 382/294 |
| 6,045,508 A * | 4/2000 | Hossack et al. | 600/447 |
| 6,148,095 A * | 11/2000 | Prause et al. | 382/131 |
| 6,245,017 B1 | 6/2001 | Hashimoto et al. | |
| 6,261,234 B1 * | 7/2001 | Lin | 600/461 |
| 6,263,089 B1 * | 7/2001 | Otsuka et al. | 382/107 |
| 6,328,693 B1 | 12/2001 | Miyatake et al. | |
| 2003/0018255 A1 * | 1/2003 | Martin et al. | 600/437 |
| 2003/0195422 A1 * | 10/2003 | Frisa et al. | 600/437 |
| 2004/0068188 A1 * | 4/2004 | Robinson | 600/447 |

FOREIGN PATENT DOCUMENTS

| | | |
|---|---|---|
| JP | 2000-237205 | 9/2000 |
| JP | 2002-369888 | 12/2002 |
| JP | 2003-144412 | 5/2003 |
| WO | WO 01/00084 | 1/2001 |

OTHER PUBLICATIONS

Theresa A Tuthill, Jonathan M. Rubin, J. B. Fowlkes: "Three-dimensional Flow Vectors from rf Ultrasound Signals", Proc. SPIE (2002), vol. 4867, No. 210, Apr. 11, 2003 pp. 210-217 XP002529692.

Chinese Office Action for Chinese Patent Application No. 201010106465.7, issued on May 2, 2012 with a partial English translation.

* cited by examiner

PROJECTIVE COMPONENT
OF MOTION VECTOR

ULTRASONIC MOTION DETECTING DEVICE, AND IMAGE PRODUCING DEVICE AND ULTRASONIC THERAPEUTIC USING THE DETECTING DEVICE

TECHNICAL FIELD

The present invention relates to a motion detecting device that detects a three-dimensional motion of an object by using ultrasonic waves, and an image producing device and a ultrasonic therapeutic device using the ultrasonic motion detecting device.

BACKGROUND ART

Attention has been paid to an extracorporeal therapy using ultrasonic waves or heavy particle beams such as HIFU (High-Intensity Focused Ultrasound) or an extracorporeal shock wave lithotripsy as a useful therapy that is low in the physical load of a patient and is capable of expecting a reduction in the therapeutic period since the invasiveness is low, and QOL (Quality of Life) after therapy is high. However, in order to conduct a low-invasive therapy, it is essential to visually perceive the motion of an object and a change with age. In particular, the motion due to the movement of a person to be examined and the motion due to a respiratory movement or peristalsis are accurately estimated, and the three-dimensional movement of the object is grasped, thereby making it possible to expect the more accurate low-invasive therapy.

Hereinafter, a description will be given of a conventional motion detecting method and a therapeutic device using the motion detecting method.

Patent Document 1 (Japanese Patent Laid-Open No. 2000-237205) has reported a method of detecting a motion and conducting an ultrasonic therapy by using an ultrasonic transducer that is attached to a mechanism which is capable of arbitrarily rotating an imaging cross-section. The method is roughly classified into a contour extraction mode and a therapeutic mode. In the contour extraction mode, a contour extraction line of an object is drawn by using an ultrasonic static image, and two or more singularities are set. It is possible to estimate the motion of the object by focusing the motion of the singularities and reconstructing the contour from the positional relationship of the singularities. The focusing of the singularities and the reconstruction of the contour are conducted on plural different cross-sections of the object, and it is confirmed that a focal point of the therapeutic ultrasonic waves exists within the contour of the object. Then, the mode is shifted to the therapeutic ultrasonic waves, and the ultrasonic waves of the energy amount of which is obtained from a cauterization volume of a therapeutic region is irradiated. The movement (motion) of the therapeutic region is estimated from the breath or motion of the patient by a vibration meter or a ultrasonic monitor, and when the motion exceeds a predetermined threshold value, the irradiation of the ultrasonic waves is automatically stopped. Then, a process of setting the focal point is again repeated.

Also, in Patent Document 2 [Japanese Patent Laid-Open No. 2002-369888], a high-resolution three-dimensional image of an object is obtained before therapy, and the object is approximated by an ellipsoidal sphere. The two-dimensional cross-sectional image (elliptical shape) of the object is imaged in real time during therapy to obtain an in-plane barycentric motion and an area change of the object. The two-dimensional motion in the imaging region of the object is estimated from the barycentric motion. Also, the most matching position of the two-dimensional cross-sectional image that is obtained from the area change in the three-dimensional image that is approximated by the ellipsoidal sphere is determined to estimate the motion in a direction perpendicular to the two-dimensional cross-sectional image. According to the method, the three-dimensional motion is detected in real time, and the irradiation of the ultrasonic waves is controlled according to the presence or absence of the object in the therapeutic beam irradiated region.

As a diagnostic image device that displays an image which is necessary for diagnosis and therapy, there are an X-ray CT device (X-ray Computed Tomography), an MRI (Magnetic Resonance Imaging) device, a PET (Positive Emission Tomography) device, and an ultrasonic imaging device. Those imaging devices have relative merits different from each other according to the imaging region and imaging environments. The ultrasonic image is superior to the image obtained by other image acquisition means in the real time property, but suffers from a problem of the resolution as a therapy support image. On the other hand, the X-ray CT device, the MRI device, and the PET device are superior in the production of the functional information and resolution although the applied regions are different from each other, but suffers from a problem of the real time property as compared with the ultrasonic image.

The motion detecting technology obtains the positional information of the imaging cross-section of the ultrasonic transducer which changes according to the motion. An image obtained by other image acquisition means which corresponds to the imaging cross-section of the ultrasonic transducer is displayed by using the motion detecting technology, thereby making it possible to produce the optimum support image for the therapy which combines the ultrasonic cross-sectional image with an image obtained by other imaging means such as MRI or the X-ray image in real time.

Hereinafter, a description will be given of a conventional image producing device using the motion detecting method.

In Patent Document 3 (Japanese Patent Laid-Open No. 2003-144412), a high-resolution MRI three-dimensional image is obtained prediagnostically. Subsequently, a two-dimensional cross-sectional image of an object is imaged by using the ultrasonic diagnostic device. A characteristic region of the object such as the contour or blood vessels is extracted from the two-dimensional cross-sectional image thus obtained. The characteristic region thus extracted is run with the MRI three-dimensional image to ascertain the best matching position, and the two-dimensional cross-section is extracted. The extracted two-dimensional cross-section is deformed so as to coincide with the characteristic region and then displayed on an image display unit. In this manner, the ultrasonic image that is imaged in real time is replaced by an MRI image with a high resolution, thereby making it possible to display the high-resolution image in real time.

Also, Patent Document 4 (Japanese Patent Laid-Open No. 9-24034) discloses a system that conducts diagnosis and therapy within a shielded room of the MRI device. A marker that is measurable in the MRI and a clinometer for measuring an angle of the imaging region are fitted onto the ultrasonic transducer to ascertain the position of the imaging cross-section due to the ultrasonic transducer. The MRI image of the ascertained cross-section is obtained and displayed on an image display unit.

Patent Document 1: Japanese Patent Laid-Open No. 2000-237205
Patent Document 2: Japanese Patent Laid-Open No. 2002-369888
Patent Document 3: Japanese Patent Laid-Open No. 2003-144412
Patent Document 4: Japanese Patent Laid-Open No. 9-24034

DISCLOSURE OF THE INVENTION

Problems to be Solved by the Invention

In the technique of Patent Document 1, since the motion that is being irradiated with the therapeutic ultrasonic waves is detected by an indirect method using a vibration meter or a ultrasonic monitor, there arises such a problem that it is difficult to accurately estimate the motion in the therapeutic region. Also, in the case where the motion of the object is large, there arises such a problem that it is difficult to set a focal point. Also, it is estimated that a deviation of the focal point readily exceeds a threshold value, and there arises such a problem that the frequent resetting is troublesome. Also, because the therapeutic region is estimated from the position of the singularities, there arises such a problem that it is difficult to conduct the precise motion estimation and therapy on the object that particularly leads to deformation. Further, because the three-dimensional imaging is conducted, there arises such a problem that the image rate is too late for the actual motion velocity.

In the technique of Patent Document 2, the motion is estimated from the three-dimensional image of the object which is obtained before therapy and the area change of the object which is estimated from the two-dimensional image that is obtained in real time. As a result, there arises such a problem that it is difficult to precisely estimate the deformation of the object. Also, from the viewpoint that the object is approximated by the elliptical shape, there are considered plural cross-sections where the motion small in the deformation is matched by the three-dimensional ellipsoidal sphere, and there arises such a problem that it is difficult to precisely detect the motion, and the misirradiation of a normal region is not reduced. Further, because the irradiation is controlled is according to the presence or absence of the object within the irradiated region, and the irradiation is repeated, there arises such a problem that a long therapeutic time is required for the therapy.

In a technique of Patent Document 3, in order to ascertain the matching position at a stage where the characteristic region that is obtained from the ultrasonic two-dimensional image is checked out against the MRI three-dimensional image, it is necessary to scan the two-dimensional image three-dimensionally. As a result, there arises such a problem that there is a drawback that the real time property is lost. Also, the actual motion of a biological body is not limited to a parallel translation but accompanies a deformation. However, the technique of Patent Document 3 is incapable of coping with the deformation.

In the technique disclosed in Patent Document 4, the imaging of the MRI image is inferior to the imaging due to the ultrasonic waves in the real time property, and there arises such a problem that it is difficult to display the real-time movement of the object on the image.

An object of the present invention is to provide a ultrasonic motion detecting device which is capable of detecting the three-dimensional motion of an object and displaying a deformation of the object and a state of the motion as a three-dimensional image in real time, and also to provide an image producing device and a ultrasonic therapeutic device using the ultrasonic motion detecting device.

Means for Solving the Problems

According to the present invention, there is provided a ultrasonic motion detecting device comprising: two transducers that transmit and receive ultrasonic waves with respect to an object and obtain a two-dimensional cross-sectional image (B mode image) of the object; an object acquisition unit that acquires orthogonal two cross-sections (hereinafter referred to as "biplane image") in which ultrasonic wave scanning surfaces by the two transducers are orthogonal to each other, and the object is positioned on an intersection line of the two cross-sections; a signal processing unit that detects three-dimensional velocity components (hereinafter referred to as "velocity components") of a motion of the object according to the biplane image; and an image display unit that displays the motion of the object as a three-dimensional image by using the velocity components in real time.

According to the present invention, there is provided an ultrasonic therapeutic device using the ultrasonic motion detecting device, which comprises: a focal point controller that allows a focusing point of therapeutic ultrasonic waves to focus on an object with the velocity components; and an image display unit that displays a real time focusing image that observes a change of the object with time in real time.

According to the present invention, there is provided an image producing device using the ultrasonic motion detecting device, which comprises: an ascertaining unit that ascertains an imaging region of ultrasonic transducers which changes with a motion of an object; an image extraction unit that extracts an image corresponding to the ascertained region from a three-dimensional image that is obtained by another image diagnostic device; and an image display unit that displays the extracted image.

Hereinafter, a description will be given of the features of the ultrasonic motion detecting device (1) according to the present invention.

The ultrasonic motion detecting device comprises first and second ultrasonic transducers having piezoelectric elements arranged in an array, which transmit ultrasonic waves to an object and acquire reflection signals from the object; a motion detection unit that extracts an estimation region which is used for estimating a motion of the object from the reflection signals that are acquired by the first and second ultrasonic transducers, and detects a three-dimensional motion within the estimation region; and an image display unit that displays the three-dimensional motion within the estimation region, wherein ultrasonic wave scanning surfaces due to the first and second ultrasonic transducers cross over each other. In addition, the ultrasonic motion detecting device (1) has the following features (2) to (8).

(2) In the ultrasonic motion detecting device, the first and second transducers alternately conduct ultrasonic scanning to acquire a biplane image including two scanning surfaces which are not in parallel to each other.

(3) In the ultrasonic motion detecting device, the first and second transducers alternately transmit and receive ultrasonic beams to acquire a biplane image.

(4) In the ultrasonic motion detecting device, the signal component used for estimating the motion comprises a contour component of the object, a speckle component occurring by allowing the reflection signals from point reflectors that are scattered within a body of the object to interfere with each other, or a combination of the contour component with the speckle component.

(5) In the ultrasonic motion detecting device, plural estimation regions are set to estimate the partial motions of the object to detect the shift and/or deformation of an inspection region within the object.

(6) In the ultrasonic motion detecting device, a correlation function of plural one-dimensional signals of the reflection signals that are acquired by the first and second ultrasonic transducers is conducted within the estimation region.

(7) In the ultrasonic motion detecting device, the motion estimation is conducted on the respective biplane images consisting of the two scanning surfaces to detect the velocity components of the three-dimensional motion of the object.

(8) In the ultrasonic motion detecting device, the imaging cross-section is changed according to the motion of the object to display the focusing image of the object on the image display unit in real time.

According to the present invention, there is provided an ultrasonic therapeutic device that combines therapeutic transducers with the ultrasonic motion detecting device (1), wherein a focal point of the therapeutic ultrasonic waves of the ultrasonic therapeutic device focuses on the motion of the object. In the ultrasonic therapeutic device, the three-dimensional motion of the object and an automatic focusing state of the focal point of the therapeutic ultrasonic waves in correspondence with the three-dimensional motion are displayed on the image display unit as a three-dimensional real moving image, and the biplane images of the object is displayed on the image display unit at the same time.

According to the present invention, there is provided an image producing device using the ultrasonic motion detecting device (1), the image producing device (11) comprising: an imaging cross-section ascertaining unit that estimates a relative motion from an initial position of the imaging cross-section due to the first and second ultrasonic transducers according to the result of the motion that is detected by the motion detection unit to determine the positions of the imaging regions produced by the first and second ultrasonic transducers; a three-dimensional image memory unit that stores the three-dimensional image of the object therein; an initial cross-sectional position setting unit that sets a two-dimensional image that is extracted from the three-dimensional image which corresponds to the initial position as an initial position; and an image extraction unit that changes the extracted cross-section which is set by the initial cross-sectional position setting unit according to a change in the imaging cross-section due to the first and second ultrasonic transducers which is ascertained by the imaging cross-section ascertaining unit to extract a corresponding two-dimensional high-resolution image from the three-dimensional image memory unit, wherein the extracted image is displayed on the image display unit as needed. In addition, the image producing device (11) has the following features (12) to (17).

(12) In the image producing device, the three-dimensional image comprises any one of an MRI image, an X-ray CT image, and a PET image.

(13) In the image producing device, an initial position of the imaging cross-section due to the first and second ultrasonic transducers and an initial position in the three-dimensional image in correspondence with the initial position of the image cross-section are set by using positional information on a characteristic region of the object such as xiphoid process of the sternum.

(14) In the image producing device, the three-dimensional image includes an image of an artificial contrast material that is attached to an interior or an exterior of the object, and an initial position of the imaging cross-section due to the first and second ultrasonic transducers and an initial position in the three-dimensional image in correspondence with the initial position of the image cross-section are set on the basis of a position of the contrast material.

(15) In the image producing device, an initial position of the imaging cross-section due to the first and second ultrasonic transducers and an initial position in the three-dimensional image in correspondence with the initial position of the image cross-section are set at a position where an integration value of an absolute value of a difference value between the ultrasonic image due to the first and second ultrasonic transducers and the extracted image that is extracted from the three-dimensional image becomes smallest.

(16) In the image producing device, plural estimation regions are set to estimate the motion of the object, thereby detecting a shift and/or a deformation of an inspection region in the interior of the object.

(17) In the image producing device, there is provided further an extracted image reconstruction unit that sets plural estimation regions to interpolate the plural extracted cross-sections to continuously combine the estimation regions with each other, and reconstructs the two-dimensional extracted image.

Effects of the Invention

According to the ultrasonic motion detecting device of the present invention, the three-dimensional motion in the inspection region can be estimated in real time with a simple structure. Also, it is possible that the focal point of the therapeutic ultrasonic waves focuses on the shift of the therapeutic region by using the motion estimation result. The display of the focusing image makes it possible to visually observe a change of the object with time and to conduct an accurate low-invasive therapy. Also, it is possible to estimate the position of the imaging cross-section of the ultrasonic transducers which changes according to the motion from the motion estimation result. An effective image from another image diagnostic device in correspondence with the imaging cross-section is displayed, thereby making it possible to subject a patient to optimum diagnosis and therapy.

BEST MODES FOR CARRYING OUT THE INVENTION

In the ultrasonic motion detecting device according to the present invention, the biplane image of the object due to the two ultrasonic transducers is measured by a device that is simple in the structure, thereby making it possible to estimate the three-dimensional motion of the inspection region in real time. In the ultrasonic motion detecting device according to the present invention, the three-dimensional velocity components of the motion of the object can be detected with a simple structure, and the motion of the object can be displayed as the three-dimensional image in real time. Also, the real-time focusing image of the object can be displayed so as to find the change of the object with time at the same time.

Also, the focal point (therapeutic region) of the therapeutic ultrasonic waves of the ultrasonic therapeutic device is automatically focused on the motion of the object by using the ultrasonic motion detecting device, to thereby structure a ultrasonic therapeutic device that conducts an accurate and simple low-invasive therapy. In the ultrasonic therapeutic device using the ultrasonic motion detecting device according to the present invention, the focal point of the ultrasonic waves focuses on the therapeutic region according to the motion, and the therapeutic ultrasonic waves are continuously irradiated, thereby making it possible to conduct an accurate short-time therapy. Also, the change of the therapeutic region with time is displayed, thereby making it possible to suspend the irradiation of the therapeutic ultrasonic waves at an optimum timing.

Also, the position of the transducer imaging cross-section is ascertained by using the ultrasonic motion detecting device to structure the image producing device that extracts a corresponding image from the three-dimensional image that has been already obtained by another image diagnostic device, and then displays the extracted image. It is possible to provide the image producing device that ascertains the imaging region of the ultrasonic transducers in real time, which change according to the motion, by using the ultrasonic motion detecting device. The cross-section corresponding to the ascertained imaging region is extracted from the three-dimensional image obtained by another image diagnostic device, and displayed, and the effective image can be displayed in real time.

Embodiment 1

FIG. 1 is a block diagram showing the structure of an ultrasonic motion detecting device according to an embodiment 1.

FIG. 2 is a diagram showing the structure of transducers that obtain biplanes in a ultrasonic motion detecting device according to the embodiment 1. Hereinafter, the structure that obtains a biplane image will be described with reference to FIGS. 1 and 2.

A ultrasonic transducer 13 has a structure in which plural piezoelectric elements are arranged in parallel. An analog transmitting signal is transmitted to the respective piezoelectric elements from a transmitting beamformer 11 through a D/A converter 12, and an object 10 is irradiated with the ultrasonic waves. The ultrasonic waves that are transmitted from the respective piezoelectric elements are electronically delayed by the transmitting beamformer 11, and are focused with a given depth. The transmitting signal is reflected within the object 10, and again received by the respective piezoelectric elements of the ultrasonic transducer. The reflective echoes that have been received by the respective piezoelectric elements are converted into digital signals by an A/D converter 15, and then transmitted to a receiving beamformer 16 after the amount of attenuation that changes according to the arrival depth of the transmitting waves has been corrected by a TGC (Time Gain Controller) unit 14. The receiving beamformer 16 multiplies the digital signals by delay times corresponding to distances between the focal position and the respective piezoelectric elements, and outputs the addition results. The focused ultrasonic waves are two-dimensionally scanned to obtain a two-dimensional reflective echo distribution of the object 10. An RF signal that is separated into a real part and an imaginary part is outputted from the receiving beamformer 16, and then converted into a video signal (raw signal) by an envelope detector 17. The outputted video signal is subjected to correction between the respective scanning lines by a scan converter 18, and then reconstructed into the two-dimensional image data. Thereafter, the two-dimensional image data is displayed on an image display 19.

The RF signal that has been outputted from the receiving beamformer is transmitted to a motion detector 20 that estimates the quantitative estimation of a three-dimensional motion. In addition, the motion estimation results are transmitted to an imaging region controller 21 of the transducer to change the imaging cross-section of the transducer 13.

The imaging cross-section can be changed by the following methods. A first method is a method of fitting a mechanism that mechanically moves the transducer 13. The transducer 13 is moved on the basis of the motion detection result so that the object can be always positioned in an oblique settable region. A second method is a method of using the transducer 13 having a two-dimensional array. Since the two-dimensional oblique can be set in the two-dimensional array, it is possible to focus on the object without moving the transducer 13 having the two-dimensional array.

As the transducer 13 having the above function, as shown in FIG. 2, transducers 30 and 31 that image the biplane images are arranged in a T-bone, and alternately scan ultrasonic waves to image the two-dimensional cross-sectional image, thereby making it possible to acquire the intended biplane images. In this example, the arrangement of the T-bone is exemplified. However, the present invention is not limited to this example if the biplane images are obtained. For example, it is possible to arrange the transducers in a cross shape. Also, since an arbitrary biplane image can be imaged by using the transducer having the two-dimensional array, the transducer of the two-dimensional array is effective in the present invention. There is particularly no limit of the type of the transducers.

FIGS. 11A and 11B are diagrams showing the motion of an object that passes through the imaging region in the ultrasonic motion detecting device according to the embodiment 1. FIG. 11A is a diagram viewed from an X-axial direction, and FIG. 11B is a diagram viewed from a Z-axial direction. The object moves in the stated order to positions 77a, 77b, 77c, and 77d, passes through the imaging region 76, and moves out of the imaging region 76. Reference numerals 77a, 77b, 77c, and 77d denote positions to which the object is moved.

FIG. 12 shows an ultrasonic image that is obtained in correspondence with the motion of the object shown in FIG. 11 in the ultrasonic motion detecting device according to the embodiment 1.

FIG. 13 is a diagram showing a change in a one-dimensional signal waveform of an object which is obtained between adjacent frames in the ultrasonic motion detecting device according to the embodiment 1.

FIG. 3 is a diagram showing the object that moves in a three-dimensional space in the ultrasonic motion detecting device according to the embodiment 1.

FIG. 4 is a diagram showing the object that moves in a three-dimensional space and the projective component of a motion vector which is representative of the motion of the object in the ultrasonic motion detecting device according to the embodiment 1.

FIG. 5 is a graph showing a difference in the motion of the object due to angles in the ultrasonic motion detecting device according to the embodiment 1.

Hereinafter, a description will be given of a method of obtaining three-dimensional velocity components ($V_x$, $V_y$, $V_z$) of the motion from the biplane image with reference to FIGS. 11, 12, 13, 3, and 4.

In the ultrasonic motion detecting device according to the embodiment 1, the three-dimensional velocity components of the motion of the object which are positioned on the intersection line of the biplane images are obtained to estimate the motion. The imageable region due to the biplane images is limited to an x-z plane in the transducer 30 and to a y-z plane in the transducer 31 on the basis a coordinates space (x, y, z) shown in FIG. 2. As a result, the velocity components of the motion of the object which are projected onto the two planes (x-z plane, y-z plane) are detected on the biplane images.

In this example, attention is paid to a single y-z imaging region 76 shown in FIG. 11, and let us consider the motion of the object that moves in the stated order to the positions 77a, 77b, 77c, and 77d of the object that passes through the imaging region 76 out of the imaging region 76. In other words, the object moves to the object positions 77a, 77b, 77c, and 77d in the stated order, passes through the imaging region 76, and moves out of the image region 76. In this event, as shown in FIG. 12, the two-dimensional image of the object which is obtained by the imaging region 76 changes according to the motion of the object, and changes as indicated by two-dimensional images 78a, 78b, 78c, and 78d of the ultrasonic imaging region 76 at the positions 77a, 77b, 77c, and 77d of the object. Also, as shown in FIG. 12, the cross-section image of the object which is obtained by the imaging region 76 changes as indicated by two-dimensional cross-section images 79a, 79b, 79c, and 79d at the positions 77a, 77b, 77c, and 77d of the object according to the motion of the object. One-dimensional signal waveforms 81a and 81b that are extracted from an image 80 into which the two-dimensional images of the adjacent frames 78a and 78b are superimposed on each other are shown in FIG. 13. The signal waveforms 81a and 81b are signals from the two-dimensional cross-section images 79a and 79b of the object shown in FIG. 12.

In the case where the object moves out of the imaging region, the deformation of a signal waveform occurs in addition to the shift of the waveform between the adjacent frames, thereby making it difficult to estimate the motion due to the mutual correlation function. However, when the frame rate is set at a high speed so as to suppress the deformation of the signal waveform to the minimum, thereby making it possible to obtain the barycentric movement of the object, and also making it possible to estimate the projective components of the motion of the object onto the imaging region in a given time. The projective components of the velocity which is detected from the two-dimensional image are different depending on an angle between the imaging region and the motion even in the motion of the same velocity. As a result, the mutual correlation function is calculated between the adjacent frames, thereby making it possible to detect a difference in the motion which depends on the angle between the direction of the motion and the imaging region, as shown in FIG. 5. Also, a slope corresponding to the velocity components is quantitatively estimated so as to estimate the three-dimensional motion. Also, when plural regions in which the motion is estimated are set, the partial motion of the object can be estimated. As a result, the deformation of the object can be additionally estimated.

More-specifically, a process of obtaining the velocity components of the object will be described below. Three-dimensional coordinate axes are set in the biplane images, and the object that moves within a coordinates space due to the three-dimensional coordinate axes (movement from a position 40 to a position 41) is shown in FIG. 3. Reference numeral 40 indicates a position (base point) of the object which is criterial, and 41 is a position of the object that has moved. For simplification, it is assumed that θ=0, and attention is paid to the cross-section x-z to detect $V_x$. When ψ is changed to, for example, 90°, 60°, 30°, and 0°, there is a change in the motion that is detected by the angle ψ as shown in FIG. 4. A graph in which the axis of abscissa represents a time, and the axis of ordinate represents the motion is obtained as shown in FIG. 5, and the velocity components can be estimated from the slopes of the graph. Likewise, when $V_y$ and $V_z$ are found, the three-dimensional velocity components ($V_x$, $V_y$, $V_z$) of the object are found by Ex1, Ex2, and Ex3 from the three-dimensional space diagram shown in FIG. 3, thereby making it possible to estimate the three-dimensional motion. Reference V denotes an absolute value of the three-dimensional velocity component of the object.

$$V_x = V \cos \psi \sin \theta \quad (Ex1)$$

$$V_y = V \sin \phi \sin \theta \quad (Ex2)$$

$$V_z = V \cos \theta \quad (Ex3)$$

Up to now, there have been proposed several methods that capture the motion of the object by using the mutual correlation function. However, in any method, an interest is taken in only the two-dimensional motion that readily takes a correlation, and only the motion within the imaging region is estimated. In the ultrasonic motion detecting device according to the embodiment 1, the projective component of the motion of the object which is apart from the imaging region where the correlation is not taken is detected by using the biplane image which is made up of two cross-section images, thereby making it possible to estimate the three-dimensional motion.

In calculation of the velocity components, there can be two objects that take the mutual correlation. In other words, the biplane image contains a contour component of the object, and a speckle component that occurs by allowing signals reflected in various phases from fine scatterers that are scattered around the object to interfere with each other. Accordingly, the method of detecting the motion of the object can include a method of directly focusing on the contour of the object in real time (hereinafter referred to as "contour extracting method"), and a method of estimating the motion of the speckle component to indirectly estimate the motion of the object (hereinafter referred to as "speckle method"). Also, a method of combining the above two methods together is also effective in an improvement in the precision of the quantitative estimation. Both of the contour extracting method and the speckle method are required to proceed so that a change in the waveform of the structure in a region that takes the mutual correlation due to the high frequency removal is reflected by the calculation result.

Since both of the contour extracting method and the speckle method do not take the correlation in the case where the deformation of the signal waveform is large, it is necessary that the frame rate is set at a high speed, and the instantaneous motion of the object is captured to suppress the deformation of the waveform. However, in the case where the motion between the adjacent frames is smaller than the detection sensitivity due to the correlation function, the motion estimation due to the correlation function between the adjacent frames is always 0. In order to avoid this situation, the motion estimation is conducted according to a flowchart shown in FIG. 14.

FIG. 14 is a flowchart for explaining a statistical processing that is conducted in the motion estimation of the object in the ultrasonic motion detecting device according to the embodiment 1.

First, in Step 82, a frame (base frame) that is a base is set. In Step 83, a mutual correlation function is calculated between the base frame and a next frame. In Step 84, it is determined the authenticity (yes or no) of whether the motion of the object which is found by the mutual correlation function is 0, or not, and in the case where it is true (yes), the correlation function with an after next frame is calculated while holding the base frame in Step 85, and the operation is again returned to Step 84. In Step 84, in the case where it is false (no), the operation is returned to Step 82, and this frame is reset as the base frame. The steps 82 to 85 are repeated, and the motion in a given time is found to conduct the motion estimation.

Embodiment 2

Hereinafter, a description will be given of an ultrasonic therapeutic device using the ultrasonic motion detecting device according to the embodiment 1.

FIG. 6 is a flowchart for explaining the operation of the ultrasonic therapeutic device using the ultrasonic motion detecting device according to the embodiment 1.

FIG. 7 is a block diagram showing the structure of a ultrasonic therapeutic device using the ultrasonic motion detecting device according to the embodiment 1.

Hereinafter, a description will be given of a flowchart shown in FIG. 6. In Step 1, the biplane images of the object are obtained. In Step 2, an estimation region (a sub region) is set in the biplane images to conduct the setting process of the estimation region. In Step 3, the velocity components of the motion are calculated to conduct the three-dimensional motion estimation due to the function. In Step 5, the motion of the object and the focal point of the therapeutic supersonic waves (beam) are displayed as the three-dimensional image. Also, in Step 4, the therapeutic region focusing image in real time is displayed.

The structure of the device shown in FIG. 7 includes a focal point controller 22 that controls the focal point of the therapeutic ultrasonic waves in the ultrasonic therapeutic device on the basis of an output signal of the motion detector 20, and a therapeutic transducer 23 for irradiating the therapeutic ultrasonic waves in addition to the structure of the device shown in FIG. 1. The focal point controller 22 feeds the estimation results of the motion detector 20 back to the therapeutic transducer to control the focusing conditions (irradiation position, irradiation area, irradiation amount) of the therapeutic ultrasonic waves. The structural elements common to those in FIG. 1 will be omitted from the description.

The focal point of the therapeutic ultrasonic waves is allowed to focus on the motion of the object according to the calculation result of the three-dimensional motion velocity component which is obtained by the ultrasonic motion detecting device of the present invention, thereby making it possible to realize a low-invasive therapy that is simple and high in the selectivity. A conventional view point that the therapeutic region is moved in the coordinates system which is set in the ultrasonic transducer is shifted to a coordinates system in which the motion of the therapeutic region is fixed. As a result, not only the positional information of the therapeutic region is always obtained, but also the irradiation energy of the therapeutic ultrasonic waves can be estimated, thereby making it possible to implement the just enough optimum therapy even in the case where the therapeutic region is shifted. With respect to the automatic focusing of the focal point, the motion of the therapeutic transducer 23 within the region is capable of focusing on the object by controlling a delay time that is effected by the transmitting beamformer 11 and changing the focal point of the ultrasonic waves (hereinafter referred to as "oblique"). There can be several methods of focusing on the motion in a direction apart from the imaging region of the object.

As a first method, there is a method of fitting a mechanism that mechanically moving the therapeutic transducer 23. The ultrasonic transducer is moved on the basis of the motion detection result so that the object can be always positioned at an oblique settable region. Accordingly, it is unnecessary to move the transducer manually, and a healer is capable of concentrating attention on the determination of the timing at which the irradiation of the therapeutic ultrasonic waves stops while watching only a screen on which a change of the object with time is displayed. As a result, the more accurate low-invasive therapy can be executed.

As a second method, there is a method of using the therapeutic transducer 23 having a two-dimensional array. Since two-dimensional oblique of a broad region is enabled in the two-dimensional array, it is possible to focus on the object without moving the therapeutic transducer 23.

Subsequently, a description will be given of a method of displaying a three-dimensional moving image of the object in real time and an object focusing image.

FIG. 8 is a diagram showing a display example of the therapeutic region focusing image and the three-dimensional moving image at a time point in the ultrasonic therapeutic device according to the embodiment 2. In the structure of FIG. 8, the display 19 shown in FIG. 7 is made up of a therapeutic region focusing image display unit 51 and an object real-time three-dimensional moving image display unit 55. On the real-time three-dimensional moving image display unit 55 are displayed an object three-dimensional image 53 including the therapeutic region, a therapeutic ultrasonic wave focusing position 56, and an image 54 indicative of a focal point of the therapeutic ultrasonic waves. On the therapeutic region focusing image display unit 51 are displayed a biplane image 52a including a cross-section image 50a of the therapeutic region, and a biplane image 52b including a cross-section image 50b of the therapeutic region.

In the ultrasonic therapeutic device according to the embodiment 2, the three-dimensional image 53 of the object 10 including the therapeutic region which has been acquired before therapy is moved according to the obtained estimation result of the motion, and displayed on the object real-time three-dimensional moving picture display unit 55, thereby making it possible to visually observe the three-dimensional motion. Also, the image 54 indicative of a focal point of the therapeutic ultrasonic waves which indicates the positional information of the focal point 56 of the therapeutic ultrasonic waves is displayed at the same time, thereby making it possible to grasp the focal point focusing status in real time. The three-dimensional image of the object which is acquired in Step 6 is not limited to the image acquiring means. The healer is capable of more clearly grasping the positional relationship of the focal point and the therapeutic region by using the high-resolution image such as the MRI or X-ray CT image. Also, the three-dimensional image of the object due to the MRI or X-ray CT is acquired again while the irradiation of the therapeutic ultrasonic waves suspends for cooling the therapeutic region. As a result, a region that has been subjected to therapy and a region that has not yet been subjected to therapy can be displayed three-dimensionally, thereby making it possible to enhance a precision and efficiency of the therapy. Also, a change of the object with time can be observed by the biplane images during the irradiation in real time, and the irradiation can be stopped at a timing when it is determined that the therapy has been completed.

Embodiment 3

FIG. 9 is a flowchart for explaining the operation of an image producing device according to an embodiment 3. Hereinafter, a flowchart shown in FIG. 9 will be described. In Step 60, the biplane images of the object are obtained. In Step 61, an initial position (region) of an image (imaging cross-section) which is obtained in Step 60 is set. In Step 62, the motion estimation region (sub region) is set. In Step 63, the motion estimation conducted by the correlation function is conducted, and the velocity component estimation process of the motion is conducted. In Step 64, a three-dimensional image data of the object is obtained before therapy by another imaging means (for example, MRI or X-ray CT). In Step 67, an initial position of the extracted cross-section image which is extracted from the three-dimensional image acquired before therapy in Step 64 is set. In Step 68, the extracted cross-section image is relatively shifted, the reconstruction process of the extracted cross-section image is conducted in Step 69, and the reconstructed extracted image is displayed in Step 70.

FIG. 10 is a block diagram showing the image producing device according to the embodiment 3. Hereinafter, the structural elements that are common to those shown in FIG. 1 will be omitted from description.

The three-dimensional image of the object which has been acquired by another image diagnostic device such as the MRI, X-ray CT, PET, or CT in advance is stored in the three-dimensional image memory 72. Subsequently, the initial position of the ultrasonic image is set by an initial positioning unit 71 for imaging region, and an initial position of the extracted image from the three-dimensional image due to another image diagnostic device, which corresponds to the initial position of the ultrasonic image, is set in an initial positioning unit 73 for extracted image. In order to achieve the conformity of the initial position of the ultrasonic image with the initial position of the extracted image from another image diagnostic device, it is necessary to set the characteristic points by the xiphoid process of the sternum, the high luminance region of a body tissue, or a contrast material that is attached to an interior or an exterior of the object. Also, the conformity can be conducted by a method of setting the initial position at a position where an integration value of an absolute value of a difference between the images becomes minimum by using the contour information of the object.

Then, the three-dimensional motion of the object is estimated by the motion detector 20 in the same manner as that of the embodiment 1. The extracted cross-section (extracted image) is relatively moved by a deformation unit 74 on the basis of the estimation result. The extracted cross-section is reconstructed by a reconstruction unit 75, and the extracted cross-section is displayed on the display 19. In this method, since the extracted cross-section is ascertained from the relative movement with respect to the initial position which is the basis, the extracted image can be displayed without being affected by the small deformation of the inspection region.

In the case where the deformation of the inspection region is large, it is necessary to display the extracted image taking the deformation into consideration. However, it is possible to apply the above-described method to the plural estimation regions. The extracted cross-sections corresponding to the respective set estimation regions are relatively moved on the basis of the motion estimation results. Because the relative motions in the respective estimation regions are different from each other, the respective extracted cross-sections after the movement do not fall into a single plane and are dispersed. Therefore, the interpolation of those discontinuous portions is conducted by the reconstruction unit 75, and the image is reconstructed two-dimensionally, thereby making it possible to display the extracted image including the deformation.

Also, the three-dimensional image obtained by another image diagnostic device is held four-dimensionally, that is, the plural images are held on a time axis, thereby making it possible to display the image including the deformation. In this case, it is not always necessary to set plural estimation regions. After processing of the deformation unit 74, a difference between the ultrasonic image and the image information in the peripheral region of the extracted cross-section and on the time axis of the peripheral region is estimated, and the image in which an integration value of an absolute value of the difference is minimum is extracted, thereby making it possible to display the extracted image including the deformation.

INDUSTRIAL APPLICABILITY

According to the present invention, there can be provided an ultrasonic motion detecting device that is capable of detecting the three-dimensional motion of the object, and estimating the motion as the three-dimensional image in real time.

DESCRIPTION OF SYMBOLS

Figure 1:
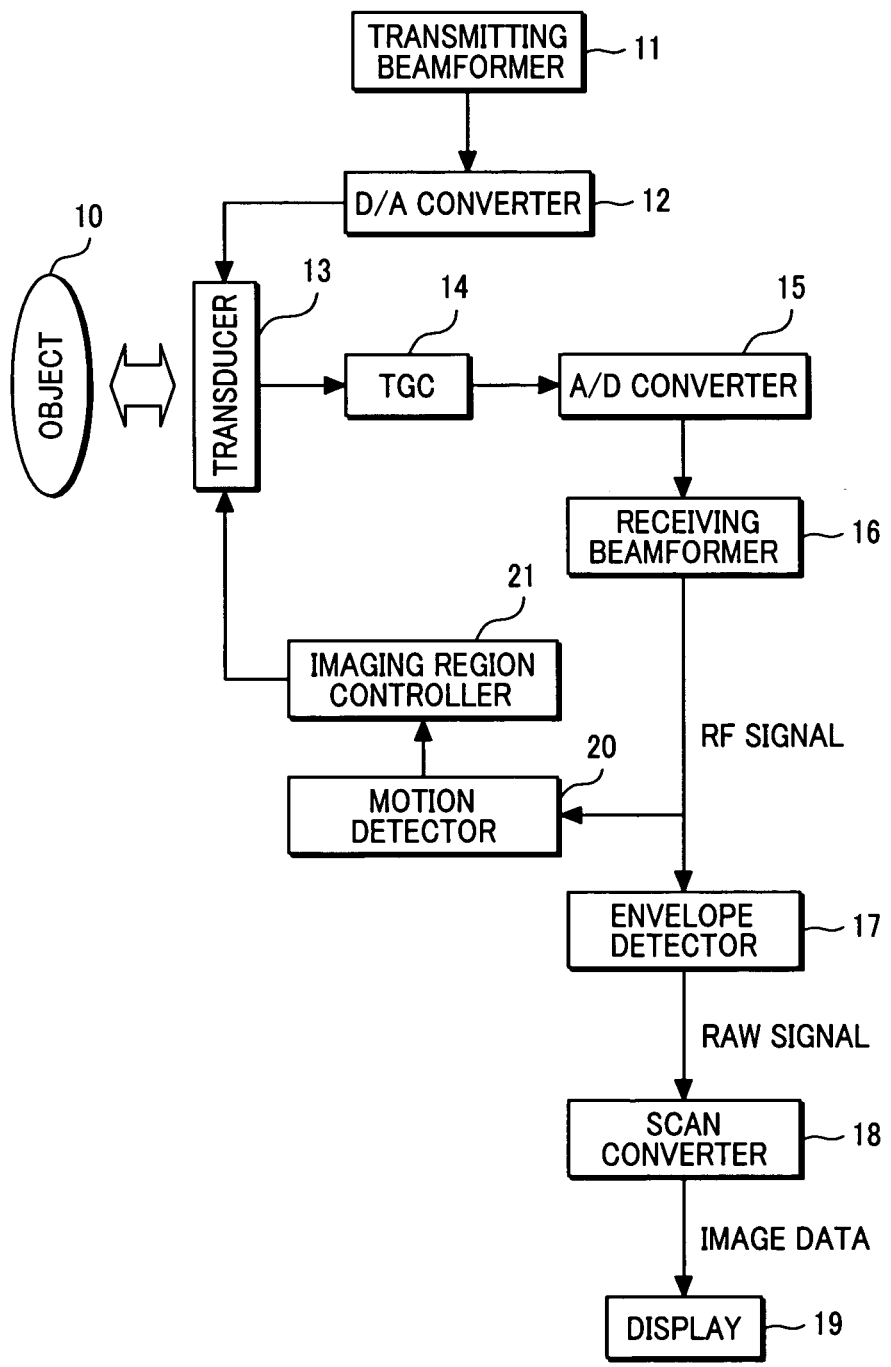
FIG. 1 is a block diagram showing the structure of an ultrasonic motion detecting device according to an embodiment 1.
Figure 2:
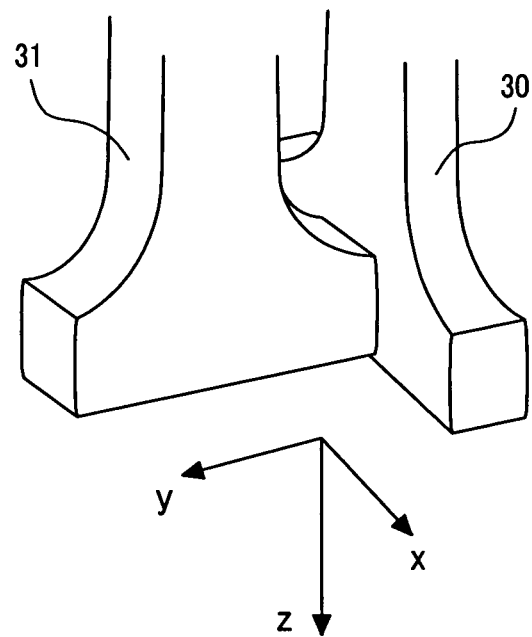
FIG. 2 is a diagram showing the structure of transducers that obtain biplanes in the ultrasonic motion detecting device according to the embodiment 1.
Figure 3:
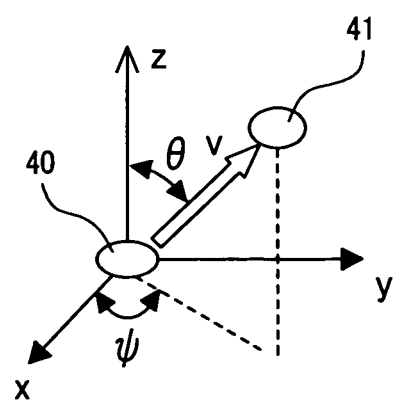
FIG. 3 is a diagram showing the object that moves in a three-dimensional space in the ultrasonic motion detecting device according to the embodiment 1.
Figure 4:
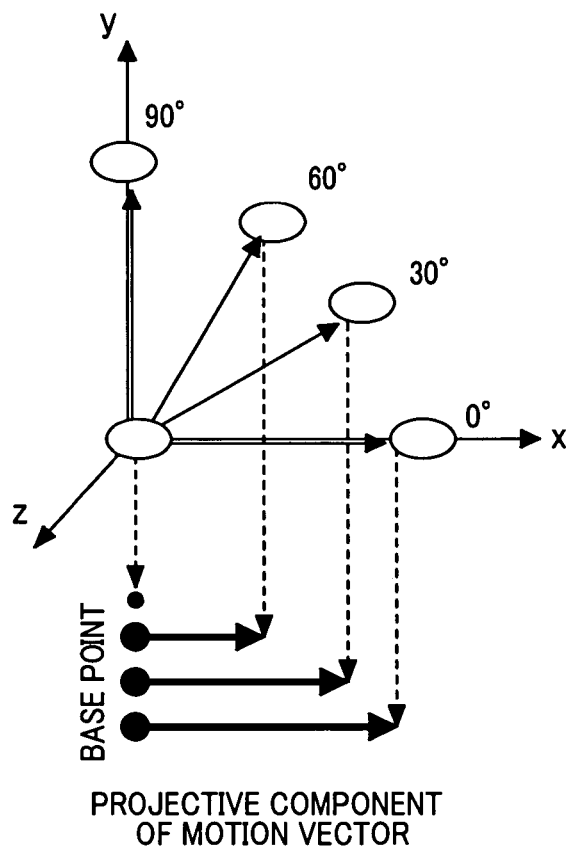
FIG. 4 is a diagram showing the object that moves in a three-dimensional space and the projective component of a motion vector which is representative of the motion of the object in the ultrasonic motion detecting device according to the embodiment 1.
Figure 5:
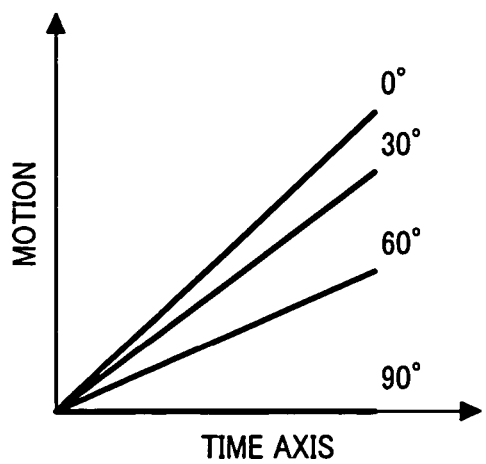
FIG. 5 is a graph showing a difference in the motion of the object due to angles in the ultrasonic motion detecting device according to the embodiment 1.
Figure 6:
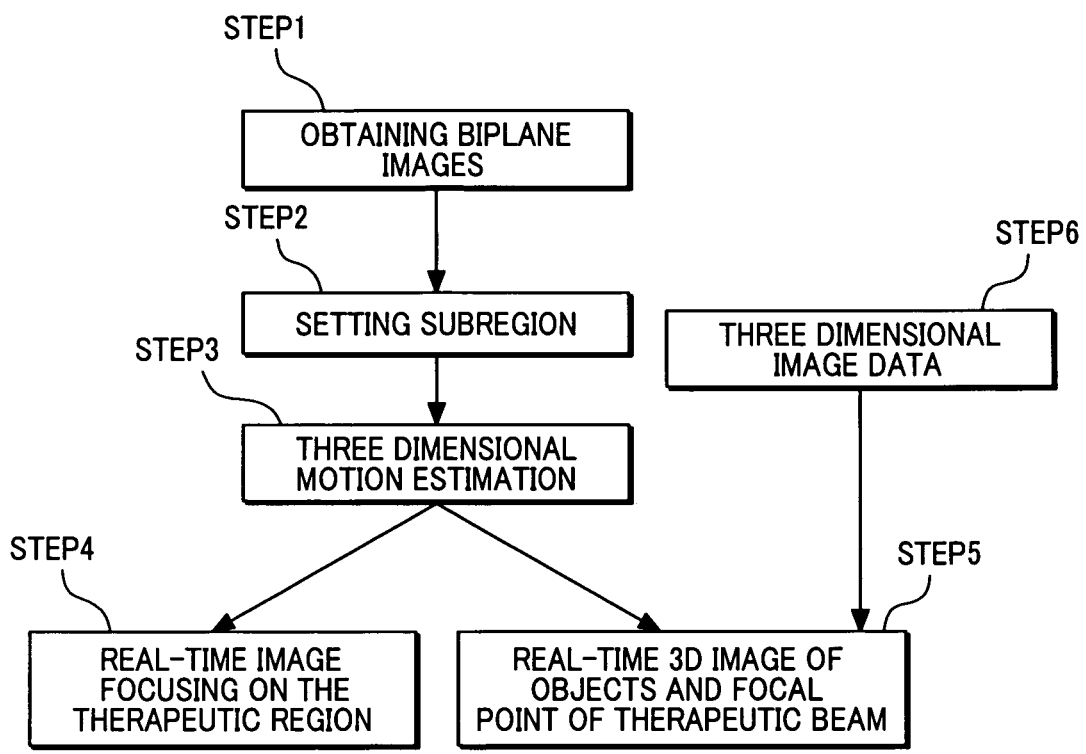
FIG. 6 is a flowchart for explaining the operation of the ultrasonic therapeutic device using the ultrasonic motion detecting device according to the embodiment 1.
Figure 7:
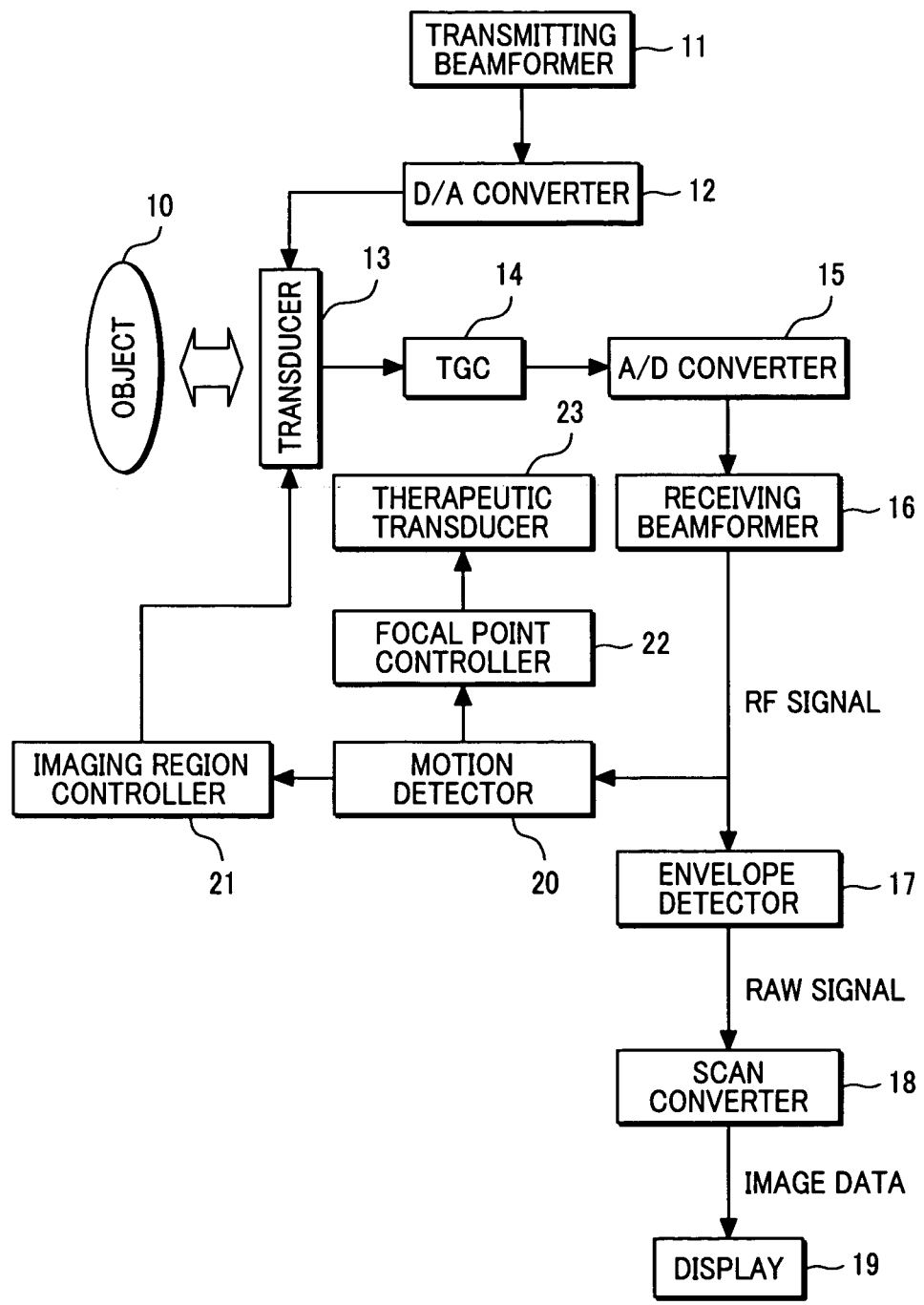
FIG. 7 is a block diagram showing the structure of a ultrasonic therapeutic device using the ultrasonic motion detecting device according to the embodiment 1.
Figure 8:
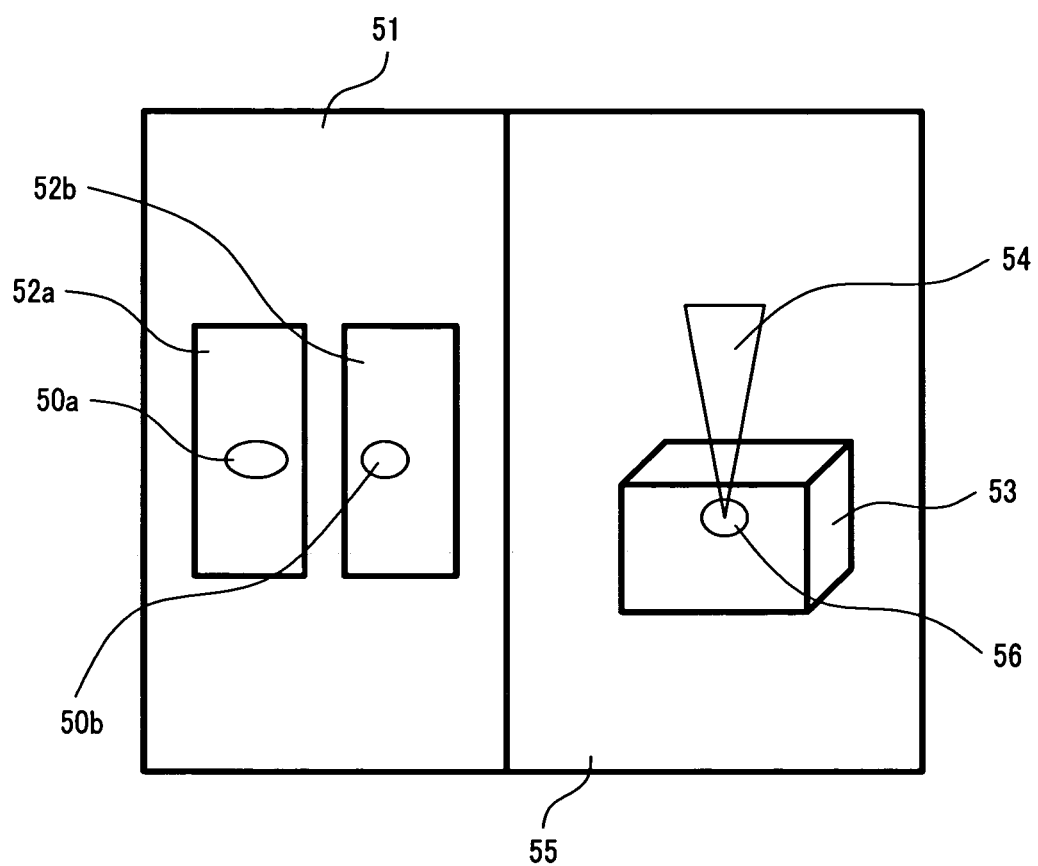
FIG. 8 is a diagram showing a display example of the therapeutic region focusing image and the three-dimensional moving image at a time point in the ultrasonic therapeutic device according to an embodiment 2.
Figure 9:
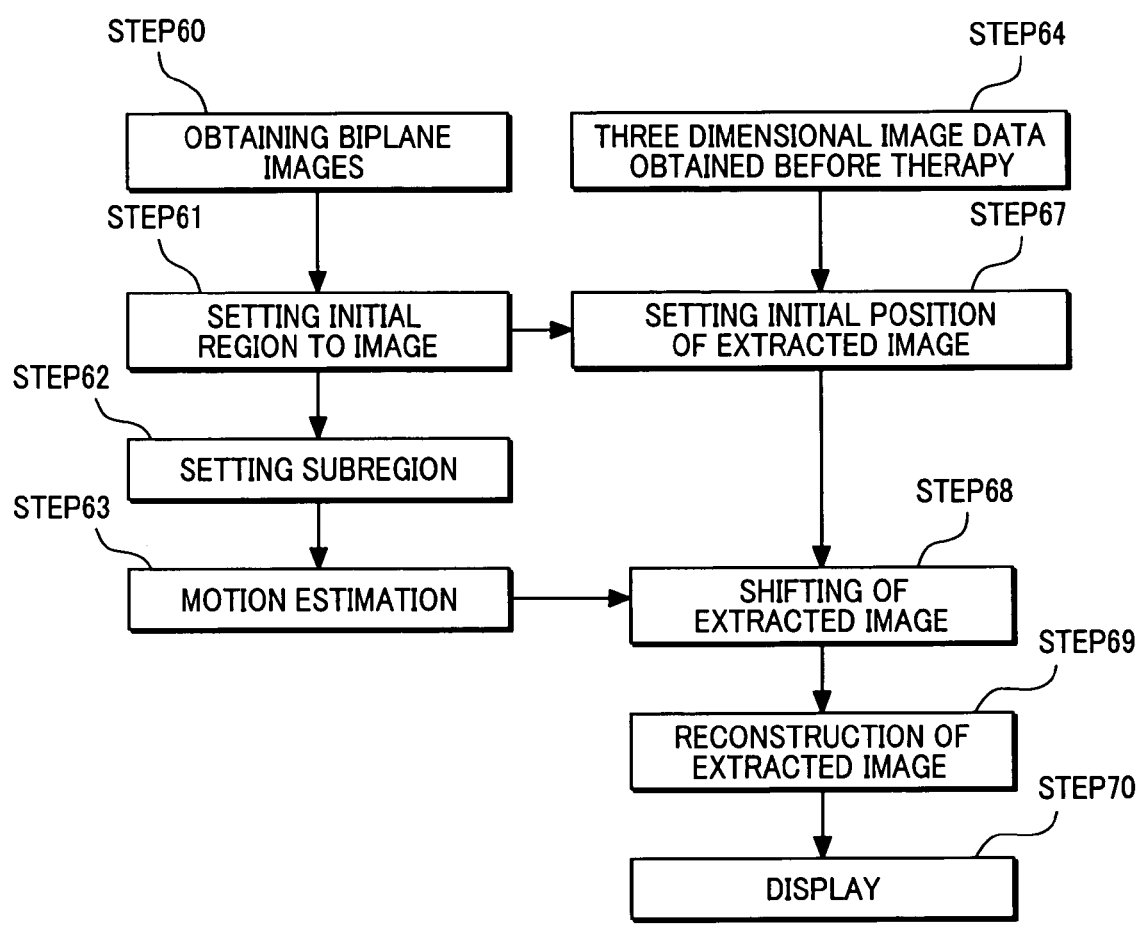
FIG. 9 is a flowchart for explaining the operation of an image producing device according to an embodiment 3.
Figure 10:
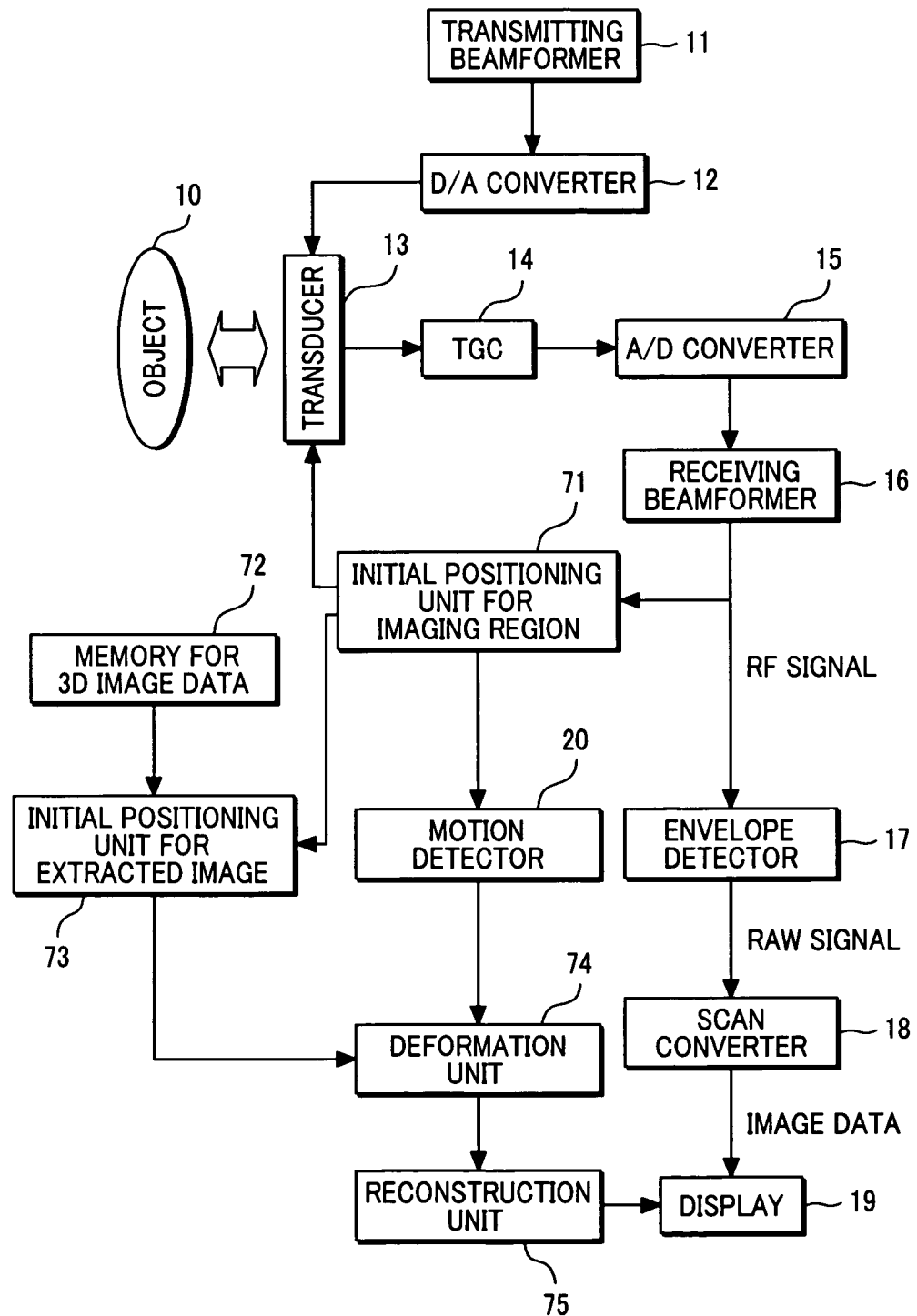
FIG. 10 is a block diagram showing the image producing device according to an embodiment 3.
Figure 11A:
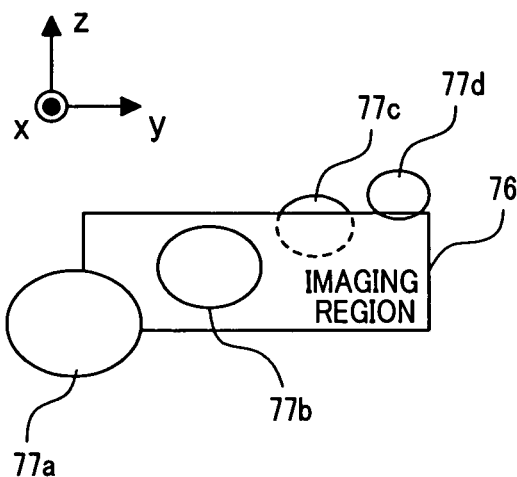
FIGS. 11A and 11B are diagrams showing the motion of an object that passes through the imaging region in the ultrasonic motion detecting device according to the embodiment 1
Figure 11B:
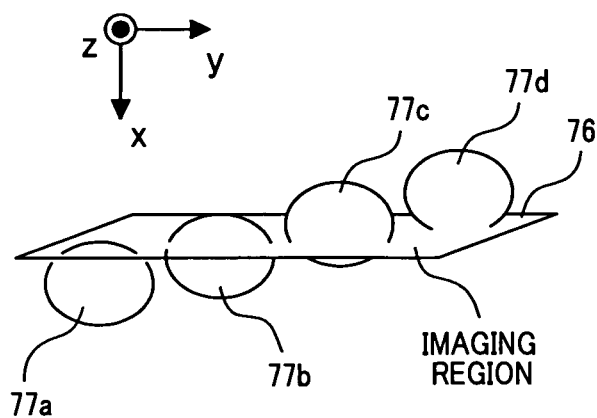
Figure 12:
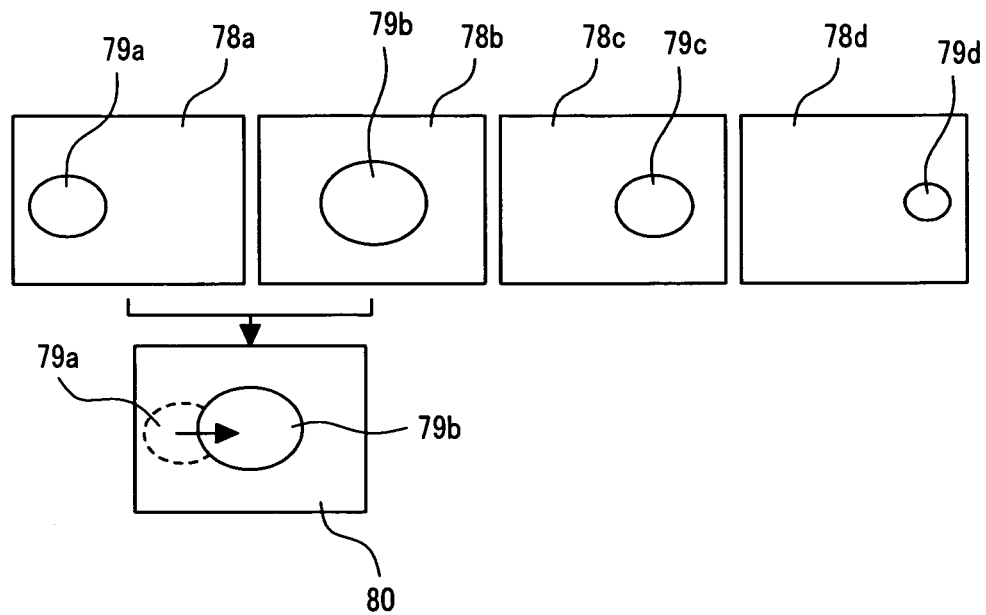
FIG. 12 shows an ultrasonic image that is obtained in correspondence with the motion of the object shown in FIG. 11 in the ultrasonic motion detecting device according to the embodiment 1.
Figure 13:
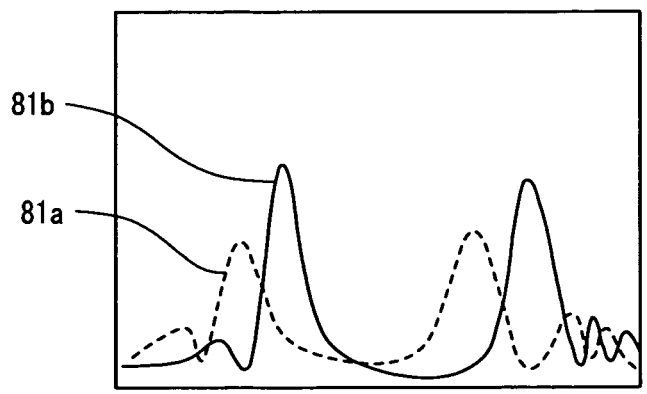
FIG. 13 is a diagram showing a change in a one-dimensional signal waveform of an object which is obtained between adjacent frames in the ultrasonic motion detecting device according to the embodiment 1.
Figure 14:
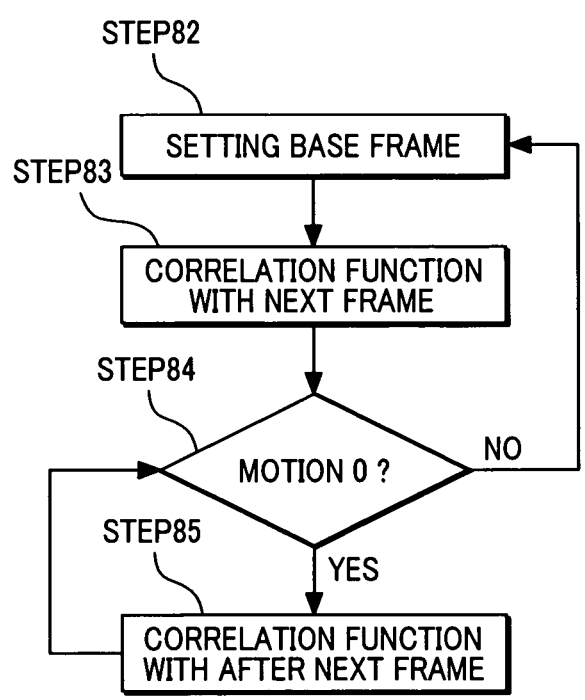
FIG. 14 is a flowchart for explaining a statistical processing that is conducted in the motion estimation of the object in the ultrasonic motion detecting device according to the embodiment 1.

Reference numeral 10 denotes an object; 11 is a transmitting beamformer; 12 is a D/A converter; 13 is a ultrasonic transducer; 14 is a time gain controller; 15 is an A/D converter; 16 is a receiving beamformer; 17 is an envelope detector; 18 is a scan converter; 19 is a display; 20 is a motion detector; 21 is an imaging region controller; 22 is a focal point controller; 23 is a therapeutic transducer; 30 and 31 are transducers that image the biplane images; 40 is a position of the object which is a basis; 41 is a position of the object after movement; 50$a$ and 50$b$ are cross-section images of a therapeutic region; 51 is a therapeutic region focusing image display unit;

52a is a biplane image including the cross-section image 50a of the therapeutic region; 52b is a biplane image including the cross-section image 50b of the therapeutic region; 53 is a three-dimensional image of the object including the therapeutic region; 54 is an image indicative of a focal point of the therapeutic ultrasonic waves; 55 is an object real-time three-dimensional moving image display unit; 56 is a therapeutic ultrasonic wave focusing position; 71 is an initial positioning unit; 72 is a three-dimensional image memory; 73 is an initial positioning unit for extracted image; 74 is a deformation unit; 75 is a reconstruction unit; 76 is a transducer imaging region; 77a, 77b, 77c, and 77d are positions of the object; 78a is a two-dimensional image of the ultrasonic imaging region 76 at the position 77a of the object; 78b is a two-dimensional image of the ultrasonic imaging region 76 at the position 77b of the object; 78c is a two-dimensional image of the ultrasonic imaging region 76 at the position 77c of the object; 78d is a two-dimensional image of the ultrasonic imaging region 76 at the position 77d of the object; 79a is a two-dimensional cross-section image that is obtained at the position 77a of the object; 79b is a two-dimensional cross-section image that is obtained at the position 77b of the object; 79c is a two-dimensional cross-section image that is obtained at the position 77c of the object; 79d is a two-dimensional cross-section image that is obtained at the position 77d of the object; 80 is an image into which the images 78a and 78b are superimposed on each other; 81a is a one-dimensional signal waveform of the image 79a; and 81b is a one-dimensional signal waveform of the image 79b.

The invention claimed is:

1. An ultrasonic motion detecting device, comprising:
an ultrasonic transducer having piezoelectric elements arranged in an array, which transmit ultrasonic waves to an object and acquire reflection signals from ultrasonic wave scanning surfaces of the object;
a motion detection unit that extracts a plurality of estimation regions which are used for estimating partial motions of the object from the reflection signals that are acquired by the ultrasonic transducer, and detects a three-dimensional motion of the object within the estimation regions;
an image display unit that displays the three-dimensional motion within the estimation regions;
an imaging cross-section ascertaining unit that estimates a relative motion from an initial position of the imaging cross-section due to the ultrasonic transducer according to the result of the motion that is detected by the motion detection unit, to determine the positions of the imaging regions produced by the ultrasonic transducer;
a three-dimensional image memory unit that stores a three-dimensional image of the object therein;
an initial cross-sectional position setting unit that sets a two-dimensional image that is extracted from the three-dimensional image which corresponds to the initial position as an initial position; and
an image extraction unit that changes the extracted cross-section which is set by the initial cross-sectional position setting unit according to a change in the imaging cross-section due to the ultrasonic transducer which is ascertained by the imaging cross-section ascertaining unit to extract a corresponding two-dimensional high-resolution image from the three-dimensional image memory unit,
wherein the ultrasonic wave scanning surfaces due to the ultrasonic transducer cross over each other;
wherein the motion detection unit detects projected components that are detected from a plurality of first two-dimensional cross-section images of one of the ultrasonic wave scanning surfaces of the object and a plurality of second two-dimensional cross-section images of another of the ultrasonic wave scanning surfaces of the object, in order to produce velocity components of the three-dimensional motion of the object which are positioned on an intersection line of the first and second two-dimensional cross-section images with mutual correlation function, and constructs the three-dimensional motion on the basis of the first two-dimensional cross-section image, the second two-dimensional cross-section image and the projected components; and
wherein the extracted image is displayed on the image display unit as needed.

2. The ultrasonic motion detecting device according to claim 1, wherein the ultrasonic transducer alternately conducts ultrasonic scanning to acquire biplane images including the ultrasonic wave scanning surfaces which are not in parallel to each other, as the first and second two-dimensional cross-section images.

3. The ultrasonic motion detecting device according to claim 1, wherein the ultrasonic transducer alternately transmits and receives ultrasonic beams to acquire the biplane images.

4. The ultrasonic motion detecting device according to claim 1, wherein the signal component used for estimating the motion comprises a contour component of the object, a speckle component occurring by allowing the reflection signals from point reflectors that are scattered within a body of the object to interfere with each other, or a combination of the contour component with the speckle component.

5. The ultrasonic motion detecting device according to claim 1,
wherein the mutual correlation function is conducted within the estimation regions.

6. The ultrasonic motion detecting device according to claim 1,
wherein the ultrasonic wave scanning surfaces are changed according to the motion of the object to display the focusing image of the object on the image display unit in real time.

7. An ultrasonic therapeutic device that combines a therapeutic transducer with the ultrasonic motion detecting device according to claim 1, wherein a focal point of the therapeutic ultrasonic waves of the ultrasonic therapeutic device focuses on the motion of the object.

8. The ultrasonic therapeutic device according to claim 7, wherein the three-dimensional motion of the object and an automatic focusing state of the focal point of the therapeutic ultrasonic waves in correspondence with the three-dimensional motion are displayed on the image display unit as a three-dimensional real moving image, and the biplane images of the object are displayed on the image display unit at the same time.

9. The image producing device according to claim 1, wherein the three-dimensional image comprises any one of an MRI image, an X-ray CT image, and a PET image.

10. The image producing device according to claim 1, wherein the initial position of the imaging cross-section due to the ultrasonic transducer and an initial position in the three-dimensional image in correspondence with the initial position of the image cross-section, are set by using positional information on a characteristic region of the object including a xiphoid process of the sternum.

11. The image producing device according to claim 1, wherein the three-dimensional image includes an image of an artificial contrast material that is attached to an interior or an exterior of the object, and the initial position of the imaging cross-section due to the ultrasonic transducer and an initial position in the three-dimensional image in correspondence with the initial position of the image cross-section, are set on the basis of a position of the contrast material.

12. The image producing device according to claim 1, wherein the initial position of the imaging cross-section due to the ultrasonic transducer and an initial position in the three-dimensional image in correspondence with the initial position of the image cross-section, are set at a position where an integration value of an absolute value of a difference value between the ultrasonic image due to the ultrasonic transducer and the extracted image that is extracted from the three-dimensional image becomes smallest.

13. The image producing device according to claim 1, wherein a plurality of estimation regions are set to estimate the motion of the object, thereby detecting a shift and/or a deformation of an inspection region in the interior of the object.

14. The image producing device according to claim 1, further comprising: an extracted image reconstruction unit that sets a plurality of estimation regions to interpolate a plurality of extracted cross-sections to continuously combine the estimation regions with each other, and reconstructs the two-dimensional extracted image.

15. The ultrasonic motion detecting device according to claim 1,
wherein the motion detection unit produces the motion of the projected component with calculating the mutual correlation function between a base frame and a next frame of sequential frames, and if the motion is lower than a predetermined value, produces the motion of the projected component with calculating the correlation function between the base frame and an after next frame of the sequential frames.

16. The ultrasonic motion detecting device according to claim 1, wherein the ultrasonic transducer is a transducer having a two dimensional array.

17. The ultrasonic motion detecting device according to claim 1,
wherein an initial position of the imaging cross-section due to the ultrasonic transducer and an initial position in the three-dimensional image in correspondence with the initial position of the image cross-section, are set by using positional information on a characteristic region of the object.

18. An ultrasonic motion detecting device, comprising:
an ultrasonic transducer, which transmits ultrasonic waves to an object and acquire reflection signals from ultrasonic wave scanning surfaces of the object;
a motion detection unit that extracts a plurality of estimation regions which are used for estimating partial motions of the object from the reflection signals that are acquired by the ultrasonic transducer, and detects a three-dimensional motion of the object within the estimation regions;
an imaging cross-section ascertaining unit that estimates a relative motion from an initial position of the imaging cross-section due to the ultrasonic transducer according to the result of the motion that is detected by the motion detection unit, to determine the positions of the imaging regions produced by the ultrasonic transducer;
a three-dimensional image memory unit that stores a three-dimensional image of the object therein;
an initial cross-sectional position setting unit that sets a two-dimensional image that is extracted from the three-dimensional image which corresponds to the initial position as an initial position; and
an image extraction unit that changes the extracted cross-section which is set by the initial cross-sectional position setting unit according to a change in the imaging cross-section due to the ultrasonic transducer which is ascertained by the imaging cross-section ascertaining unit to extract a corresponding two-dimensional high-resolution image from the three-dimensional image memory unit,
wherein the ultrasonic wave scanning surfaces due to the ultrasonic transducer cross over each other;
wherein the motion detection unit detects velocity components of the three-dimensional motion of the object, which is positioned on an intersection line of the ultrasonic waves scanning surfaces, with mutual correlation function based on first two-dimensional cross-section images of the object obtained from the ultrasonic transducer in sequential frames and second two-dimensional cross-section images of the object obtained from the ultrasonic transducer in sequential frames, and constructs the three-dimensional motion of the object to be displayed in an image display unit in accordance with the velocity components of the three-dimensional motion of the object; and
wherein the extracted image is displayed on the image display unit as needed.

19. The ultrasonic motion detecting device according to claim 18,
wherein the motion detection unit produces the motion of the object with calculating the mutual correlation function between a base frame and a next frame of the sequential frames, and if the motion is lower than a predetermined value, produces the motion of the object with calculating the correlation function between the base frame and an after next frame of the sequential frames.

20. The ultrasonic motion detecting device according to claim 18, wherein the ultrasonic transducer is a transducer having a two dimensional array.

* * * * *